US00PP34856P2

(12) United States Plant Patent
Thiede

(10) Patent No.: US PP34,856 P2
(45) Date of Patent: Dec. 20, 2022

(54) ***DIANTHUS* PLANT NAMED 'KLEDG21338'**

(50) Latin Name: ***Dianthus gratianopolitanus* Vill.**
Varietal Denomination: KLEDG21338

(71) Applicant: Klemm+Sohn GmbH & Co. KG, Stuttgart (DE)

(72) Inventor: Lena Thiede, Riederich (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 17/744,606

(22) Filed: May 13, 2022

(30) Foreign Application Priority Data

Jun. 22, 2021 (QZ) ..... PBR20211683

(51) Int. Cl.
*A01H 5/02* (2018.01)
*A01H 6/30* (2018.01)

(52) U.S. Cl.
USPC ..... Plt./277
CPC ..... *A01H 6/305* (2018.05)

(58) Field of Classification Search
USPC ..... Plt./277, 273
CPC ..... A01H 5/02
See application file for complete search history.

(56) References Cited

PUBLICATIONS

CPVO Register Consultation 4.1.68 Citation for 'KLEDG21338'; Jun. 14, 2022; 1 page.*

* cited by examiner

*Primary Examiner* — Kent L Bell
(74) *Attorney, Agent, or Firm* — Weatherly IP Solutions, LLC; Barbara Campbell

(57) ABSTRACT

A new *Dianthus* plant designated 'KLEDG21338' particularly distinguished by single dark pink flowers having red centers and red macules and an upright habit, is disclosed.

1 Drawing Sheet

Genus and species: *Dianthus gratianopolitanus* Vill.
Variety denomination: 'KLEDG21338'.

CROSS-REFERENCE TO RELATED APPLICATIONS

This application claims priority to and the benefit of Community Plant Variety Rights Application File No. 2021/1683, filed on Jun. 22, 2021, the entire contents of which are incorporated herein by reference for all purposes.

BACKGROUND OF THE NEW PLANT

The present invention comprises a new and distinct variety of *Dianthus*, botanically known as *Dianthus gratianopolitanus* Vill., and hereinafter referred to by the variety name 'KLEDG21338'. 'KLEDG21338' originated from an open-pollination of the proprietary female *Dianthus* plant 'DSS-2011-0087' (unpatented) with an un-named and unknown male parent in June 2015 in Stuttgart, Germany and in June 2016, 'KLEDG21338' was selected from a population of plants grown from the seed of the original open-pollination.

In August 2016, 'KLEDG21338' was first vegetatively propagated by vegetative stem cuttings in Stuttgart, Germany and Latina, Italy. 'KLEDG21338' was found to reproduce true to type in successive generations of asexual propagation in Latina, Italy and Stuttgart, Germany via vegetative cuttings.

SUMMARY

The following are the most outstanding and distinguishing characteristics of 'KLEDG21338' when grown under normal horticultural practices in Stuttgart, Germany.

1. Single dark pink flowers with red centers and red macules; and
2. An upright plant habit.

DESCRIPTION OF THE PHOTOGRAPH

This new *Dianthus* plant is illustrated by the accompanying photograph of a 13-week-old plant taken in March 2019 and grown in a greenhouse in Stuttgart, Germany. The colors shown are as true as can be reasonably obtained by conventional photographic procedures. The photograph is a whole plant photo of 'KLEDG21338' and shows the foliage, buds, and flowers.

DESCRIPTION

The following detailed descriptions set forth the distinctive characteristics of 'KLEDG21338'. The data which define these characteristics were collected from asexual reproductions carried out in Stuttgart, Germany. Data was collected in March 2022 from plants that were 6-months-old and grown in a plastic greenhouse. Color references are to The R.H.S. Colour Chart of The Royal Horticultural Society of London (R.H.S.), $5^{th}$ edition (2007).

Classification:

*Family*.—Caryophyllaceae.

*Botanical*.—*Dianthus gratianopolitanus* Vill.

*Designation*.—'KLEDG21338'.
*Type*.—Pot carnation.

Parentage: Female parent 'DSS-2011-0087' (unpatented).

Plant:
*Propagation type*.—Vegetative stem cuttings, terminal cuttings.
*Time to produce a rooted young plant*.—10 to 14 days.
*Root description*.—Fine; young roots are RHS 161D (Greyed-Yellow) and mature roots are RHS 199C (Grey-Brown).
*Rooting habit shape*.—Lanceolate.
*Plant form*.—Upright.
*Plant height*.—11.0 cm to 13.0 cm.
*Plant diameter or spread*.—16.0 cm to 18.0 cm.
*Hardiness*.—Winter-hardy in Germany.

Lateral branches/stems:
*Shape of the branch in cross-section*.—Circular.
*Hollowness of the branch*.—Absent.
*Length*.—5.0 cm to 8.0 cm.
*Diameter*.—3.0 cm to 4.0 cm.
*Internode length*.—2.0 cm to 2.5 cm.
*Internode quantity per branch*.—3 to 4.
*Node length*.—0.2 cm to 0.4 cm.
*Node diameter*.—0.2 cm to 0.4 cm.
*Texture*.—Smooth.
*Color*.—RHS 146B (Yellow-Green).
*Flower clustering on the lateral branch*.—None.

Foliage:
*Arrangement*.—Opposite.
*Length*.—3.5 cm to 4.0 cm.
*Width*.—0.2 cm to 0.4 cm.
*Shape*.—Lanceolate.
*Apex*.—Obtuse.
*Base*.—Acute.
*Margin*.—Entire.
*Texture* (*both upper and lower surfaces*).—Smooth.
*Cross-section of the leaf*.—Moderately concave.
*Glaucosity of the leaf*.—Weak.
*Leaf color* (*both immature and mature*).—Upper surface: RHS 138B (Green) for immature and RHS 138A (Green) for mature. Lower surface: RHS 138B (Green) for immature and RHS 138A (Green) for mature.
*Venation pattern*.—Absent.

Flowers:
*Flower type*.—Single flowers with sprays; 1 to 2 flowers per spray.
*Fragrance*.—Present.
*Position of the flowers compared to the foliage of the plant*.—Same level.
*Profile of both the upper and lower part in the lateral view*.—Upper is flat and lower is convex.
*Diameter of flower*.—2.0 cm to 2.5 cm.
*Natural flowering season*.—Spring to Autumn.
*Flower longevity on the plant*.—14 to 18 days.

Buds:
*Length*.—1.0 cm to 1.3 cm.
*Diameter*.—0.3 cm to 0.5 cm.
*Shape*.—Elliptic.
*Color*.—RHS 187A (Greyed-Purple) and RHS 147B (Yellow-Green).
*Extrusion of the styles at the bud stage*.—Absent.

Corolla:
*Quantity of petals and arrangement*.—5 and arranged in one whorl.
*Corolla height*.—0.8 cm to 1.0 cm.
*Petal length*.—2.3 cm to 2.8 cm.
*Petal width*.—0.7 cm to 1.0.
*Petal shape*.—Spoon-shaped.
*Petal apex*.—Obtuse.
*Petal base*.—Acute.
*Petal margin*.—Serrated.
*Depth of petal margin*.—Shallow.
*Petal texture* (*both upper and lower surfaces*).—Smooth.
*Petal color*.—Immature: Upper surface: RHS 53B with RHS 46A centers. Lower surface: RHS 53C. Mature: Upper surface: RHS 53B with RHS 46A centers and RHS 46A (Red) macules being 0.2 cm to 0.3 cm in width; 1 macule per petal. Lower surface: RHS 53C.
*Calyx*.—Quantity of sepals: Composed of 5 sepals. Longitudinal axis of the lobes of the calyx: Straight. Shape: Campanulate. Calyx height: 0.5 cm to 0.7 cm. Calyx diameter (at the apex): 0.3 cm to 0.4 cm. Sepal texture (both upper and lower surfaces): Smooth. Sepal color: Upper surface: RHS 189A (Greyed-Green). Lower surface: RHS 191B (Greyed-Green).
*Position of the outer lobes of the epicalyx in relation to the calyx*.—Adpressed and free.
*Apex shape of the outer lobes of the epicalyx*.—Acute.
*Tip length of the outer lobes of the epicalyx*.—0.2 cm.
*Apex shape of the inner lobes of the epicalyx*.—Acute.
*Tip length of the inner lobes of the epicalyx*.—0.2 cm.

Peduncles:
*Length*.—4.0 cm to 6.0 cm.
*Diameter*.—0.2 cm.
*Strength*.—Moderate.
*Texture*.—Smooth.
*Color*.—RHS 147B (Yellow-Green).

Reproductive organs:
*Stamens*.—Quantity per flower: Low (less than two). Filament length: 0.3 cm. Filament color: RHS 8D (Yellow). Anther length: 0.1 cm. Anther diameter: 0.05 cm. Anther color: RHS 18C (Yellow-Orange). Pollen amount: Sparse. Pollen color: RHS 65D.
*Pistils*.—Quantity per flower: 2. Length: 0.8 cm to 1.0 cm. Diameter: 0.05 cm. Stigma: Color: RHS 61A (Red-Purple). Shape: Curved. Length: 0.3 cm to 0.5 cm. Diameter: 0.05 cm. Style: Color: RHS 155C (White). Length: 0.3 cm. Diameter: 0.05 cm. Ovary: Color: RHS 145C (Yellow-Green). Width: 0.2 cm. Length: 0.5 cm to 0.7 cm. Shape: Oblong.

Fruit and seed set: Observed but no information is available.

Disease and pest/insect resistance: No disease and pest/insect resistance observed.

COMPARISON OF 'KLEDG21338' WITH PARENTAL LINE AND KNOWN VARIETY

'KLEDG21338' is distinguished from the female parent as described in Table 1.

TABLE 1

Comparison with Parental Line

| Characteristic | 'KLEDG21338' | Female Parent 'DSS-2011-0087' |
|---|---|---|
| Flower color | Dark pink with red centers and red macules | Red |

'KLEDG21338' can be compared to the commercial *Dianthus* variety 'KLEDG14178' (U.S. Plant Pat. No. 27,905). Differences between the varieties are described in Table 2.

TABLE 2

Comparison with Similar Variety

| Characteristic | 'KLEDG21338' | 'KLEDG14178' |
|---|---|---|
| Number of flowers per spray | 1 to 2 | 3 to 4 |
| Plant height | 11.0 cm to 13.0 cm | 10.0 cm |
| Position of the flowers compared to the foliage of the plant | Same level | Slightly above the foliage |

I claim:

1. A new and distinct variety of *Dianthus* plant designated 'KLEDG21338' as illustrated and described herein.

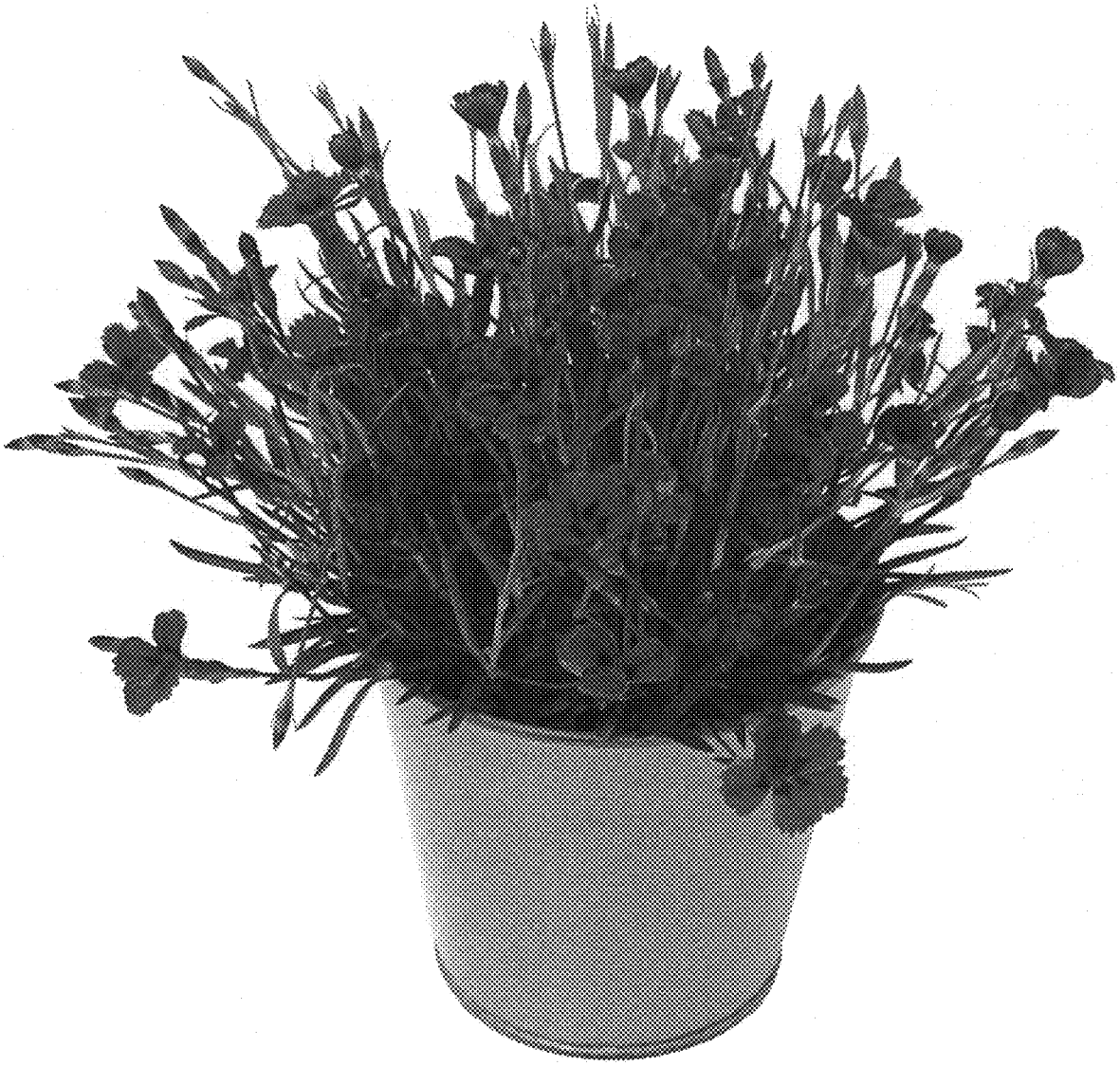

* * * * *